(12) United States Patent
Fritz et al.

(10) Patent No.: US 10,426,924 B2
(45) Date of Patent: Oct. 1, 2019

(54) PLACEMENT AID FOR PLACING A CATHETER FOR DIABETICS

(71) Applicant: MEDIZINISCHE UNIVERSITÄT GRAZ, Graz (AT)

(72) Inventors: Martin Fritz, Kobenz (AT); Christian Wüster, Villach (AT); Werner Regittnig, Graz (AT)

(73) Assignee: Medizinische Universität Graz, Graz (AT)

( * ) Notice: Subject to any disclaimer, the term of this patent is extended or adjusted under 35 U.S.C. 154(b) by 526 days.

(21) Appl. No.: 15/168,935

(22) Filed: May 31, 2016

(65) Prior Publication Data

US 2016/0345876 A1 Dec. 1, 2016

Related U.S. Application Data

(63) Continuation of application No. PCT/EP2014/072499, filed on Oct. 21, 2014.

(30) Foreign Application Priority Data

Nov. 28, 2013 (DE) ........................ 10 2013 224 431

(51) Int. Cl.
 *A61M 25/01* (2006.01)
 *A61M 5/158* (2006.01)
 (Continued)

(52) U.S. Cl.
 CPC ..... *A61M 25/0102* (2013.01); *A61B 5/14503* (2013.01); *A61B 5/14532* (2013.01);
 (Continued)

(58) Field of Classification Search
 CPC ... A61B 5/6849; A61M 5/16836; A61M 5/46; A61M 2005/14252; A61M 2005/14256;
 (Continued)

(56) References Cited

U.S. PATENT DOCUMENTS

| 2007/0078322 | A1 | 4/2007 | Stafford |
| 2008/0051714 | A1* | 2/2008 | Moberg ............... A61M 5/1413 604/135 |

(Continued)

FOREIGN PATENT DOCUMENTS

| CA | 2 338 255 A1 | 2/2000 |
| DE | 699 11 976 T2 | 8/2004 |

(Continued)

*Primary Examiner* — Kami A Bosworth
(74) *Attorney, Agent, or Firm* — Lewis Roca Rothgerber Christie LLP

(57) ABSTRACT

A placement aid for placing a catheter and a sensor wire into a body including a replacement device arranged in an interchangeable and replaceable manner having a main body, a placement needle, a catheter and a sensor wire. The placement needle is arranged within the catheter so that a tip of the placement needle protrudes from an end of the catheter along a puncturing direction and penetrates the skin when the catheter is inserted along the puncturing direction to generate a skin opening through which the catheter can be guided up to a subcutaneous final position. The sensor wire is arranged in the placement needle when the catheter is inserted along the puncturing direction and when the subcutaneous final position of the catheter is reached, the placement needle can be withdrawn from the catheter against the puncturing direction and the sensor wire remains in the catheter.

19 Claims, 11 Drawing Sheets

(51) Int. Cl.
*A61B 5/145* (2006.01)
*A61B 5/15* (2006.01)
*A61B 5/153* (2006.01)
*A61M 39/02* (2006.01)
*A61B 5/00* (2006.01)
*A61M 5/142* (2006.01)
*A61M 16/06* (2006.01)
*A61B 5/155* (2006.01)
*A61M 25/00* (2006.01)
*A61M 25/06* (2006.01)

(52) U.S. Cl.
CPC .......... *A61B 5/15003* (2013.01); *A61B 5/153* (2013.01); *A61B 5/150412* (2013.01); *A61B 5/150503* (2013.01); *A61B 5/150656* (2013.01); *A61B 5/6852* (2013.01); *A61M 5/14276* (2013.01); *A61M 5/158* (2013.01); *A61M 16/0605* (2014.02); *A61M 16/0633* (2014.02); *A61M 39/02* (2013.01); *A61B 5/155* (2013.01); *A61M 25/00* (2013.01); *A61M 25/01* (2013.01); *A61M 25/0606* (2013.01); *A61M 2005/1583* (2013.01); *A61M 2005/1585* (2013.01); *A61M 2205/0272* (2013.01); *A61M 2205/0283* (2013.01)

(58) Field of Classification Search
CPC .......... A61M 2005/14284; A61M 2005/1585; A61M 25/0102; A61M 25/0606; A61M 25/0631; A61M 25/065; A61M 2025/0002; A61M 2025/0166; A61M 2205/3303
See application file for complete search history.

(56) References Cited

U.S. PATENT DOCUMENTS

| | | |
|---|---|---|
| 2008/0086042 A1 | 4/2008 | Brister et al. |
| 2008/0319414 A1* | 12/2008 | Yodfat ................. A61B 5/6849 604/506 |
| 2009/0048563 A1 | 2/2009 | Ethelfeld et al. |
| 2009/0062767 A1* | 3/2009 | Van Antwerp ....... A61B 5/6846 604/504 |
| 2009/0099521 A1* | 4/2009 | Gravesen .......... A61M 5/14248 604/136 |
| 2011/0054400 A1* | 3/2011 | Chong ............. A61M 5/14248 604/131 |
| 2011/0319728 A1* | 12/2011 | Petisce ............... A61B 5/14503 600/309 |
| 2012/0022344 A1 | 1/2012 | Kube |
| 2013/0060233 A1* | 3/2013 | O'Connor ............ A61M 5/158 604/506 |
| 2016/0114136 A1 | 4/2016 | Woehr |
| 2016/0243302 A1* | 8/2016 | Gym ..................... A61M 5/158 |

FOREIGN PATENT DOCUMENTS

| | | |
|---|---|---|
| DE | 20 2009 009 602 U1 | 1/2010 |
| EP | 2 201 968 A1 | 6/2010 |
| WO | WO 2006/061354 A1 | 6/2006 |
| WO | WO 2008/065646 A1 | 6/2008 |

* cited by examiner

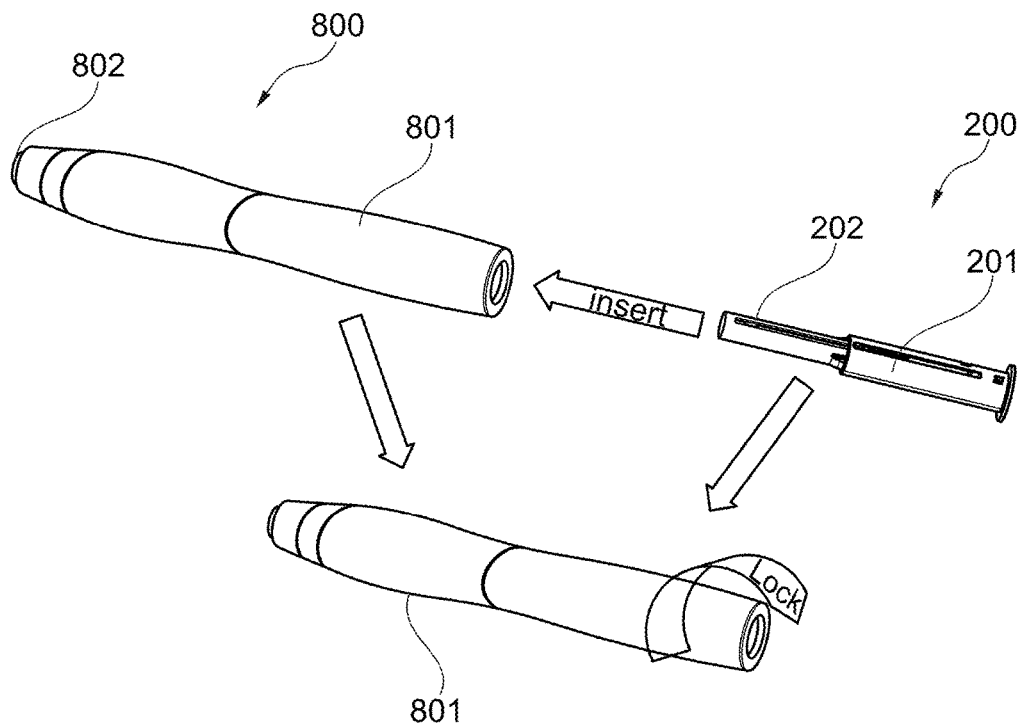
Fig. 16
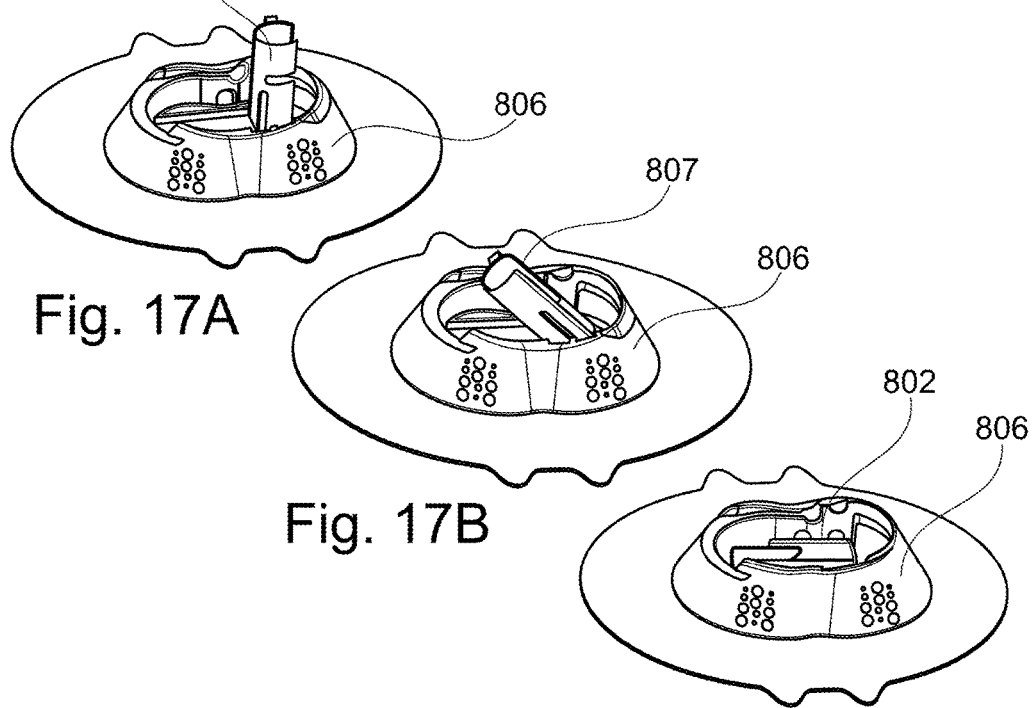
Fig. 17A
Fig. 17B
Fig. 17C

PLACEMENT AID FOR PLACING A CATHETER FOR DIABETICS

CROSS-REFERENCE TO RELATED APPLICATION(S)

This Application is a Continuation of International Application Number PCT/EP20141072499, filed on Oct. 21, 2014, which claims priority to and the benefit of German Patent Application Number 10 2013 224 431.2, filed Nov. 28, 2013, the entire contents of all of which are incorporated herein by reference.

TECHNICAL FIELD

Embodiments of the present invention relate to a placement aid and method of placing a catheter and a sensor wire into a body.

BACKGROUND

Patients with diabetes have to have the content of glucose in their blood measured frequently, several times per day for example. On the basis of this, a corresponding dose of insulin is administered. In doing so, with the aid of a needle the skin is punctured and the emerging blood is applied to a measuring strip as part of a measuring system. After the measurement has been obtained the insulin dose is calculated, wherein the insulin is injected by means of a further needle into a tissue of the patient. Several punctures of the skin are therefore necessary. In order to reduce the frequency of puncturing and the pain and discomforts associated therewith, a catheter can be implanted in the body over a longer period. Via this catheter (known as an indwelling catheter) a medication (e.g. insulin) can be administered, tissue fluid can be removed for glucose determination and/or by means of a sensor located on the catheter the glucose can be continuously measured.

DESCRIPTION

There may be a need to provide a simple, user-friendly placement aid for placing a catheter and a sensor wire.

This need is solved by means of a placement aid and a method of placing a catheter and a sensor wire into a body in accordance with the independent claims.

According to a first aspect of the present invention, a placement aid for placing (introducing) a catheter and a sensor wire into a body is provided. The placement aid comprises a placement device and a replacement device (a replacement set or infusion set so to say). The replacement device comprises a main body for application to the skin of the body, a placement needle and a sensor wire. The replacement device is arranged in an interchangeable/replaceable manner in the placement device. The placement needle is coupled to the main body. The placement needle and the catheter are arranged in relation to each other in such a way that a tip of the placement needle protrudes from a proximal end of the catheter along a puncturing direction, so that upon placing the catheter along the puncturing direction the tip of the placement needle penetrates the skin in order to produce a skin opening through which the catheter can be guided up to a subcutaneous end position in the skin or tissue. The sensor wire is coupled to the placement needle in such a way that upon placement of the catheter along the puncturing direction the sensor wire is arranged in the placement needle and that upon reaching the subcutaneous end position of the catheter the placement needle can be removed from the catheter against the puncturing direction and the sensor wire remains in the catheter.

Thereby, the catheter is detachably coupled to the placement needle so that upon reaching the sub-cutaneous end position of the catheter the placement needle can be removed from the catheter against the puncturing direction, whereas the catheter stays in the subcutaneous end position.

According to a further aspect of the present invention, a placement aid for placing (introducing) a catheter into a body is provided. In an exemplary embodiment the replacement device further comprises a piston and a needle holder, to which the placement needle is attached.

The piston is arranged in the main body in a moveable manner. The catheter is coupled by means of the placement needle to the main body in a (directly or indirectly) detachable manner in such a way that upon reaching the subcutaneous end position of the catheter the placement needle can be pulled out from the catheter contrary to the puncturing direction and the catheter remains in the subcutaneous end position. The needle holder with the placement needle is movably arranged at the main body in the puncturing direction, wherein the needle holder is coupled to the catheter so that when placing the catheter the needle holder advances the catheter forwards along the puncturing direction. The piston is coupled to the needle holder in such a way that by means of the piston the needle holder can be advanced along the puncturing direction.

In accordance with a further aspect of the present invention a method of placing a catheter and a sensor wire into a body by means of the above-described placement aid is described. The replacement device is inserted into/arranged at the placement device. The placement aid is placed on the skin of the body. The catheter is placed by way of the placement aid. The replacement device is then removed and replaced. Subsequently, a new, unused replacement device, for instance, can be newly inserted in the same placement device.

According to a further example form of embodiment of the method, a main body is applied to the skin of the body, wherein a placement needle is coupled to the main body and wherein the placement needle and a catheter are arranged with regard to each other in such a way that the placement needle is arranged within the catheter and that a tip of the placement needle protrudes from a proximal end of the catheter along the puncturing direction. The skin is penetrated with the tip of the placement needle when placing the catheter along the puncturing direction in order to produce a skin opening through which the catheter can be retraced up to a subcutaneous end position. Upon reaching the subcutaneous end position of the catheter the placement needle is removed from the catheter against the puncturing direction. According to a further aspect a needle holder with the placement needle is arranged at the main body movably along the puncturing direction, wherein the needle holder is coupled to the catheter in such a way that upon placement of the catheter the needle holder advances the catheter along the puncturing direction. A piston is coupled to the needle holder in such a way that by means of the piston the needle holder can be advanced along the puncturing direction.

Used as the catheter is, for example, a needle made of metal or plastic for example. The catheter can also be a thin tube through which a medication, e.g. insulin can be infused, bodily fluids removed and/or in which a sensor wire can be positioned. In the removed fluids or at the place of placement of the sensor wire various substances or values can be measured, such as, for example, glucose, lactate, oxygen, pH value, electrolytes. Insulin, or insulin analogues, glucagon, growth hormones can be supplied as medications.

The placement aid in accordance with embodiments of the invention can be used in human medicine as well as in veterinary medicine.

The placement needle comprises a needle which is made, for example, of metal or a similar hard material. The placement needle can be designed in a massive manner as a solid body, or have a hollow profile. The placement needle can further comprise an open hollow profile, such as a U-profile for instance. The placement needle comprises a tip which, for example, comprises a cutting edge at the distal end. The placement needle causes a small cut in the skin in order to produce a skin opening. The skin opening is expanded or torn open further by means of the remainder of the placement needle and the subsequently guided catheter. The placement needle comprises a smaller circumference than the internal diameter of the catheter so that the placement needle can be guided within the catheter.

Understood as the puncturing direction in the following is the direction along which the elements of the placement aid, for example the catheter, the placement needle and the main body, move during the application or the placement of the catheter, at least until the subcutaneous end position is reached.

The subcutaneous end position describes the desired point or puncturing depth of the catheter or the sensor wire. Depending on the application, the subcutaneous end position can be selected so that the end of the catheter or sensor wire is present in the fatty tissue, the muscle tissue or within a blood vessel.

The catheter comprises a proximal, i.e. close to the skin, end. The proximal end of the catheter describes the deepest position of the catheter in the tissue when the catheter has reached the subcutaneous end position. From this proximal end of the catheter the tip of the placement needle usually protrudes, so that during the placement of the catheter along the puncturing direction, the tip of the placement needle penetrates the skin and subsequently in a further movement the catheter is guided along the puncturing direction.

The catheter and the sensor wire are indirectly coupled by the placement needle to the main body, at least until the subcutaneous end position is reached. After the catheter and sensor wire have reached the sub-cutaneous end position the placement needle together with the main body is decoupled from the catheter and the sensor wire and can be removed from the catheter and sensor wire. In other words, after reaching the subcutaneous end position, the catheter and sensor wire on the one hand, and the main body with the placement needle on the other hand are decoupled or can be decoupled from each other.

The main body can, for example, be a hollow cylindrical body or a hollow-cylindrical tube, wherein the catheter, the sensor wire and the placement needle are arranged within the main body. The placement needle can be arranged spatially fixed to the main body or arranged in a displaceable manner at the main body. If the placement needle is spatially fixed to the main body the user can manually move the main body together with the placement needle, the sensor wire and the catheter in the puncturing direction in order to puncture the skin until the subcutaneous end position is reached. For example, the replacement device can be manually, or, as will be described below, automatically moved by means of a spring system in the puncturing direction in order to puncture the skin.

The needle holder comprises, for example, a larger diameter than the catheter or the fastening region of the catheter, so that when pushing the needle holder along the puncturing direction the needle holder comes into contact with the fastening region of the catheter and pushes it further in the puncturing direction. Accordingly, the needle holder can move against the puncturing direction without pushing the catheter against the puncturing direction. The needle holder can be made of the same material as the placement needle or can comprise a different material than the placement needle. For example, the placement needle can be made of a metallic material whereas the needle holder can be made of a plastically or elastically deformable synthetic material.

The piston is set up to press against the needle holder and advance it along the puncturing direction. The piston can, for example, comprise a cylindrical profile. In an example form of embodiment the piston has a hollow cylindrical profile. For instance, in one example form of embodiment the piston can be telescopically moved into and out from the main body. The piston can, for instance, be pushed into the main body by the user during placement of the catheter. Additionally, a further (for example spring-based) displacement mechanism can be used which presses the piston into the main body during the placement of the catheter and sensor wire. If the placement needle is movably arranged on the main body, a displacement mechanism can be used. The user applies the main body onto the skin and activates the displacement mechanism so that the placement needle, together with the catheter and the sensor wire, is moved in the puncturing direction until the subcutaneous end position is reached. The displacement mechanism is based, for example, on a spring-based mechanism, which will be explained below in exemplary forms of embodiment.

According to embodiments of the present invention the catheter is coupled to the placement needle in such a way that upon reaching the subcutaneous end position of the catheter the placement needle can be pulled out of the catheter against the puncturing direction and the catheter remains in the subcutaneous end position. The placement needle can be coupled to the catheter by means of an interlocking connection (e.g. with a hook or snap-type connection). The interlocking connection is automatically released, e.g. upon reaching the subcutaneous end position, or released by means of an unlocking mechanism which can be operated by the user, for example. Additionally the placement needle can be coupled to the catheter by means of a force-fitted connection, wherein the placement needle is coupled to the catheter by way of frictional forces. When pulling out the placement needle the retracting force acting against the puncturing direction exceeds the frictional force so that the placement needle detaches from the catheter and can be pulled out. At the same time the force-fit connection between the catheter and the issue surrounding the catheter is stronger than the retracting force so that the catheter remains in the subcutaneous end position.

The sensor wire can, for example, be rigid, i.e. plastically deformable, elastically deformable or deformable like string or non-rigid. The sensor wire forms, for example, one or more electrodes so that the sensor wire can be a component of an electrochemical sensor system. The sensor wire can be coupled to a sensor read-out unit so that in-vivo measurements can be carried out. By means of the sensor wire, on the basis of electrochemical, enzymatic, optical, gravimetric and/or calorimetric measuring principles, the concentration of analytes in tissue fluids or blood can be measured, for example the blood glucose concentration.

Furthermore, several sensor wires can be arranged in the placement needle and remain in the catheter after pulling out the placement needle. Each of the sensor wires constitutes a sensor electrode for example.

The sensor wire is held in position, for example, by means of an force-fitting connection in the placement needle during the placement of the catheter. For example, the sensor wire can be pressed with a certain pressure force against inner surface of the placement needle so that a frictional force fixes the sensor wire to the placement needle. When pulling out the placement needle the retracting force exceeds the friction for fixing the sensor wire to the placement needle so that the placement needle can be pulled out from the body relative to the sensor wire and the sensor wire remains in the subcutaneous end position.

The replacement set can thus be manipulated by the user, while the piston and the main body are protected in the inside of the placement device. The replacement device, more particularly the cannula (or the catheter), the sensor wire, the placement needle, the piston and, for example, the main body can be designed in the form of a (sterile) disposable component. This means that after one-off puncturing of the skin by the placement needle and placing the catheter and the sensor wire into the subcutaneous end position, the replacement device (e.g. the main device and the piston together with the placement needle) can be changed. A new replacement device with a new placement needle, a new sensor wire and a new catheter can again be used for renewed puncturing in the placement aid.

The placement aid can be manually operated in that the patient moves the placement device with the replacement device in the direction of the body's skin and penetrates the skin. Additionally, the placement device can, for example, be placed on the skin and the piston pressed manually in the direction of the skin by the patient in order to puncture the skin.

Furthermore, in the placement device a displacement mechanism for moving the piston, the placement needle, the sensor wire and the catheter, as described below, can be arranged. The placement device with the displacement mechanism can thus be used for a number of punctures or for a number of placement procedures. The replacement device is, for example, designed as, for example, a disposable device (comprising, among other things, the main body and the piston as disposable components). In this way, for example, more expensive and more exclusive materials can be used for the placement device, while more inexpensive disposable materials are used for the piston and the main body. In this way a placement aid can be provided which exhibits a high quality at comparatively lower prices.

With the placement aid in accordance with embodiments of the invention it is also possible for the patient to place a catheter in a simple, user-friendly way. By means of the placement device according to embodiments of the invention a placement needle initially punctures the skin in a manner that is gentle to the skin and the catheter with a larger diameter than the placement needle is then subsequently guided in. The subsequent guiding in of the catheter and the pulling out of the placement needle is made possible with a simple placement aid operating step, so that a simple operation is possible.

As described above, in accordance with a further example of embodiment the catheter and the placement needle can be designed in such a way that the placement needle and the catheter can be coupled by means of a force-fitting connection.

For example, according to a further example of embodiment of the invention the catheter can have a fastening section and a subcutaneous section. The subcutaneous section can at least partially penetrate through the skin opening in the skin, wherein the fastening section of the connection forms the interlocking or force-fitting connection with the placement needle.

The subcutaneous section describes for example the hose-like or needle-like projection of the catheter which is inserted into the tissue. The fastening section of the catheter is the section which projects outwards from the skin surface. The fastening section comprises, for example, a funnel shape in parts. The fastening section can comprise a much larger diameter than the subcutaneous section. As set out in the introduction, the fastening section is for creating the force-fitting connection with the placement needle. The fastening section can also be used for connecting with, for example, sensor read-out units, insulin pumps or other functional devices. The fastening section and the subcutaneous sections can also be made of different materials. For example, the subcutaneous section can consist of a flexible hose material for instance, whereas the fastening section is made of a hard, non-deformable, such as a hard plastic or metal.

A membrane or a clamping element made, for example, from an elastic element such as an elastic synthetic material (e.g. a silicone pad or silicone) can be arranged in the fastening section. Elastomer synthetic materials can also be elastically deformed through tension or pressure loading but thereafter they return back into their original non-deformed shape.

For example, the placement needle can pierce the membrane so that the elastic membrane is elastically deformed and presses against the placement needle with a predetermined adhesive force. In this way a force-fitting connection between the placement needle and the catheter is produced. Upon pulling out the placement needle from the clamping element the predetermined adhesive force is exceeded and the catheter remains in the subcutaneous end position.

In accordance with a further example form of embodiment the placement aid comprises a first spring which is arranged on the main body and the needle holder in such a way that a first spring force of the first spring acts along the puncturing direction in order to advance the needle holder along the puncturing direction relative to the main body upon placement of the catheter.

The first spring can be a tension spring or a pressure spring. By way of the spring an embodiment of the above-described displacement mechanism can be provided.

According to a further example of embodiment the piston is further detachably coupled with the needle holder in such a way that upon reaching the subcutaneous end position the needle holder can be decoupled from the piston and the needle holder can be moved relative to the piston along the puncturing direction.

In this way the piston can be moved along the puncturing direction with the needle holder up to the subcutaneous end position. The needle holder can therefore be guided linearly along the piston. More particularly, the placement needle, the catheter, the main body and the piston are arranged concentrically to each other along a common axis. Upon reaching the sub-cutaneous end position the piston can remain in its place, while the needle holder can, independently from the piston, be moved along the puncturing direction relative to the piston.

In an example form of embodiment the piston is in the form of a hollow profile, for example a hollow cylindrical profile. In this way, after reaching the sub-cutaneous end position, the needle holder, together with the needle, can move contrary to the puncturing direction and relative to the piston, so that the needle holder together with the needle can be pushed into the inside of the piston. Before placement, the placement needle and the catheter are located inside the piston. After placement of the catheter only the placement needle and, for example, the holding-down rod, described below for example, are located within the piston.

The piston thus forms a protective container for the used placement needle. This provides good protection against infection, for example.

Described below, as an example, is a displacement mechanism for moving the replacement device, e.g. including the piston, the placement needle, the sensor wire and the catheter, relative to the placement device.

According to an example form of embodiment the placement further comprises a second spring, which is arranged between the placement device and the needle holder in such a way that a second spring force acts along the puncturing direction in order to, during the placement of the catheter, advance the needle holder along the puncturing direction directly (or indirectly by means, for example, of the piston). The second spring can be a tension spring or a pressure spring.

In accordance with a further example form of embodiment the second spring is set up in such a way that when moving the needle holder against the puncturing direction the second spring is pre-tensioned. If, for example, the needle holder together with the piston and/or the main body is inserted into the placement device, during the placement procedure into the placement device the second spring can be automatically pre-tensioned. In this way the placement aid is simply loaded and is ready for use.

In accordance with another example form of embodiment, the placement device comprises a locking element and a trigger element. The locking element locks the needle holder in an initial position in which the second spring is pre-tensioned. The trigger element is coupled to the locking element in such a way that upon activation of the trigger element, by a user example, the locking element releases the needle holder and by way of the second spring force the needle holder can be advanced along the puncturing direction.

The locking element can, for example, hold the needle holder in the initial position by means of an interlocking or force-fitted activation mechanism. A locking element with an interlocking activation mechanism comprises, for example, corresponding locking hooks which engage in corresponding locking groove of the needle holder. The trigger element is, for example a push button or a slide control which can be operated and moved by the user. The trigger element then decouples the needle holder from the locking element so that the needle holder can be driven along the puncturing direction, on the basis of the second spring force for example.

According to a further example of embodiment the placement aid also comprises a return spring which is arranged between the placement device (or the main body) and the needle holder in such a way that a return force of the return spring acts contrary to the puncturing direction in order, after placement of the catheter and sensor wire, to advance the needle holder against the puncturing direction while the catheter and sensor wire remain in the subcutaneous end position.

By using the return spring the placement needle is automatically decoupled from the catheter and sensor wire and is withdrawn from the body contrary to the puncturing direction. In interaction with the first or second spring an automatic placement mechanism is provided. The user only has to operate the trigger element, for example, in order to activate the placement aid. After operation of the trigger element the needle holder with the needle, together with the catheter and senor wire, moves to the subcutaneous end position. The needle holder is then pulled out from the body by means of the return spring without the user having to take further steps.

In accordance with a further example form of embodiment the return spring is set up/designed in such a way that upon displacement of the needle holder along the puncturing direction the return spring is or becomes pre-tensioned. The return spring is, for example, coupled to the needle holder and is thus pre-tensioned when the needle holder moves along the puncturing direction. The second spring and the return spring are designed so that the second spring force is large enough to push the placement needle with the sensor wire and the catheter into the tissue and also pre-tension the return spring.

According to a further example form of embodiment the placement aid further comprises a holding-down rod which is movably arranged on the placement needle. The holding-down rod is designed to press the sensor wire against the placement needle or against the inner surface of the placement needle in a frictional manner. The holding-down rod is also arranged movably along the puncturing direction on the main body so that a) upon placement (moving) of the catheter along the puncturing direction the placement needle, the sensor wire and the holding-down rod can be jointly advanced to the subcutaneous end position in the skin, and that b) on reaching the subcutaneous end position of the catheter and sensor wire, the holding-down road can be pulled out from the catheter, and thus from the body, contrary to the puncturing direction.

The holding-down rod is, for example, rigid and arranged within the placement needle. The holding-down rod reduces, so to say, the free volume of the placement needle so that the sensor wire or the sensor wires are clamped between the holding-down rod and the inner surface of the placement needle. The holding-down rod thus constitutes the pressing force of the sensor wire to the inner surface of the placement needle. More particularly, in this way the placement needle can be withdrawn from the body without the holding-down rod and sensor wire being pulled out, wherein these remain in the subcutaneous end position. Only after the placement needle has been at least partially retracted from the body the holding-down rod can be removed from the body in a subsequent procedure and only the sensor wire together with the catheter remains in the body.

This staggered removal of the placement needle and the holding-down rod can be implemented with the following example form of embodiment. According to a further example form of embodiment the holding-down rod has a plunger (or a clamping ring) which is mounted to the piston by means of a frictional connection. The plunger is also arranged on the piston in such a way that in a predetermined position in the piston the needle holder presses against the plunger contrary to the puncturing direction in such a way that the frictional connection between the piston and the plunger can be overcome and the plunger with the holding-down rod can be moved by means of the needle holder contrary to the puncturing direction relative to the piston.

The predetermined position of the plunger in the piston is selected in such a way that the needle holder initially pulls the placement needle out from the body and only pushes against the plunger after the needle holder has already been moved a certain distance against the puncturing direction in the piston. After a contact between the plunger and the needle holder has been established, the needle holder pushes/pulls the plunger against the puncturing direction and the placement needle is withdrawn from the body along with the holding-down rod.

Therefore, the holding-down rod initially together with the sensor wire remains in the subcutaneous end position in the body, whereas a section of the placement needle has already been pulled out from the body. This has the advantage that the frictional force between the sensor wire and the inner surface is already sharply reduced if part of the placement needle has already been withdrawn from the body. Without the placement needle there is no force-fitting connection between the sensor wire and the holding-down rod so that the holding-down rod (after the partial withdrawal of the placement needle) can be pulled out without problems without the sensor wire essentially leaving the subcutaneous end position.

According to a further example form of embodiment the placement aid has a support element which can be attached to the skin. The main body can be detachably fasted to the support element in such a way that the main body can be fixed with a predetermined puncturing angle between the placement needle and skin surface.

The support element can, for example, be attached to the skin by means of an adhesive connection (e.g. by means of a plaster). The support element comprises, for example, coupling elements, which couple the main body to the support element in a replaceable manner. For example, the main body can be mounted to the support element by means of a bayonet fastening or by means of other interlocking or force-fitting connections (e.g. click-type connection or press fitting).

Further, the coupling element can also be adjustably mounted to the support element so that a puncturing angle can be adjusted. A puncturing angle defines the angle between the skin surface and the placement needle. The puncturing angle is, for example, between 0° and 90°. The shallower the angle the closer the subcutaneous end position is to the skin surface. The steeper the angle, for example around 90°, the deeper the subcutaneous end position is in the interior of the skin or tissue. Because of being able to select the puncturing angle the user can adapt the puncturing angle to the thickness of his/her subcutaneous fat layer so that with a given catheter and sensor wire length the proximal ends of the catheter and sensor wire can come to lie in the fatty tissue and not in the underlying muscle tissue. The replacement set can thereby be made up of a single catheter and sensor wire length.

In accordance with a further example form of embodiment the support element comprises a fastening element which is designed to fasten the catheter to the support element when the subcutaneous end position of the catheter is reached.

The fastening element forms an interlinking or a force-fitting connection with the catheter. For example, the fastening element can form a bayonet connection with the catheter. Thus, for example, the fastening element can be a bolt or pin and the catheter can, particularly in the fastening region, can have a guide groove for forming the bayonet connections. In this way the main body, together with the catheter, can be brought into position on the support element and then, after disconnection of the main body from the catheter, the main body can be removed.

As described above, after reaching the subcutaneous end position, the catheter is disconnected from the main body and detached, wherein the catheter continues to remain fixed to the support element and can be separated from the main body.

After the catheter and the sensor wire have been brought into the subcutaneous end position and fastened to the support element, the catheter and sensor wire can be used for further applications. For example, a sensor read-out unit can be attached to the sensor wire or a pump unit attached to the catheter for the infusion of medication.

Accordingly, the placement aid can have a read-out unit, for example, which can be attached to the support element in a replaceable manner so that the sensor read-out unit is coupled to the sensor wire, located in the catheter, for the purpose of signal exchange. Additionally, in a further example form of embodiment the placement aid can comprises a pump unit for the infusion of a medication, for example insulin. The pump unit is mounted to the support element in a replaceable manner such that the pump element is coupled to the catheter so that a medication can be infused by the pump unit into the catheter and thus conveyed to the subcutaneous end position.

With the placement aid according to embodiments of the invention the user can simply, for example by means of a simple activation step (for example by pressing a button or manually), insert a catheter, including a sensor wire, into the tissue, wherein by means of the used placement needle the skin is gently punctured. As the placement needle and, for example, the holding-down rod are withdrawn from the skin and stored in the piston, infection protection for used needles and holding-down rods is provided at the same time. The replacement device, comprising, for example, the piston, the placement needle, the catheter, the sensor wire and the main body, can be used in a replaceable manner in the placement device so that a disposable mechanism with sterile disposable components can be created. The main body and the piston can be produced as disposable components and fastened in the placement device in a selectively replaceable manner depending on the use.

By means of the coupling with the sterile replacement device, the placement device can be reused, wherein the contained components, i.e. the placement device and, functionally related, the components of the replacement device, can be automatically tensioned and released.

Thus, for example, according to a further aspect of the present invention, a method of placing a catheter in a body with the above-described placement aid can be implemented. According to the method, the replacement device is arranged in the placement device (in a replaceable manner). The placement aid is placed on the skin of the body and the catheter is inserted by means of the placement aid/placement device. The replacement device is then removed from the placement device. For a following placement procedure a new replacement device can be inserted into the placement device and a new placement procedure, as described above, can be carried out. The placement device and, for example, the trigger mechanism (e.g. the second spring) integrated in the placement device, can be used several times.

It is pointed out that the forms of embodiment described here do only show a limited selection of possible forms of embodiment of the invention. It is thus possible to suitably combine the features of individual forms of embodiment with each other, so that with the explicit variants of embodiment presented here, for a person skilled in the art a large variety of different forms of embodiment is considered to be clearly disclosed.

BRIEF DESCRIPTION OF THE DRAWINGS

Below, for further explanation and for a better understanding of the present invention, forms of embodiment are described in more detail with reference to the attached figures. In these

FIG. 16 shows a schematic representation of a fastening of a placement device with a main body and a piston of a replacement device in accordance with an example form of embodiment of the present invention, and FIG. 17A to FIG. 17C show schematic views of a support element with an adjustable catheter holder.

DETAILED DESCRIPTION OF EXAMPLE FORMS OF EMBODIMENT

Identical or similar components are given the same reference numbers in the Figures. The views in the Figures are schematic and are not to scale.

Figure 1:
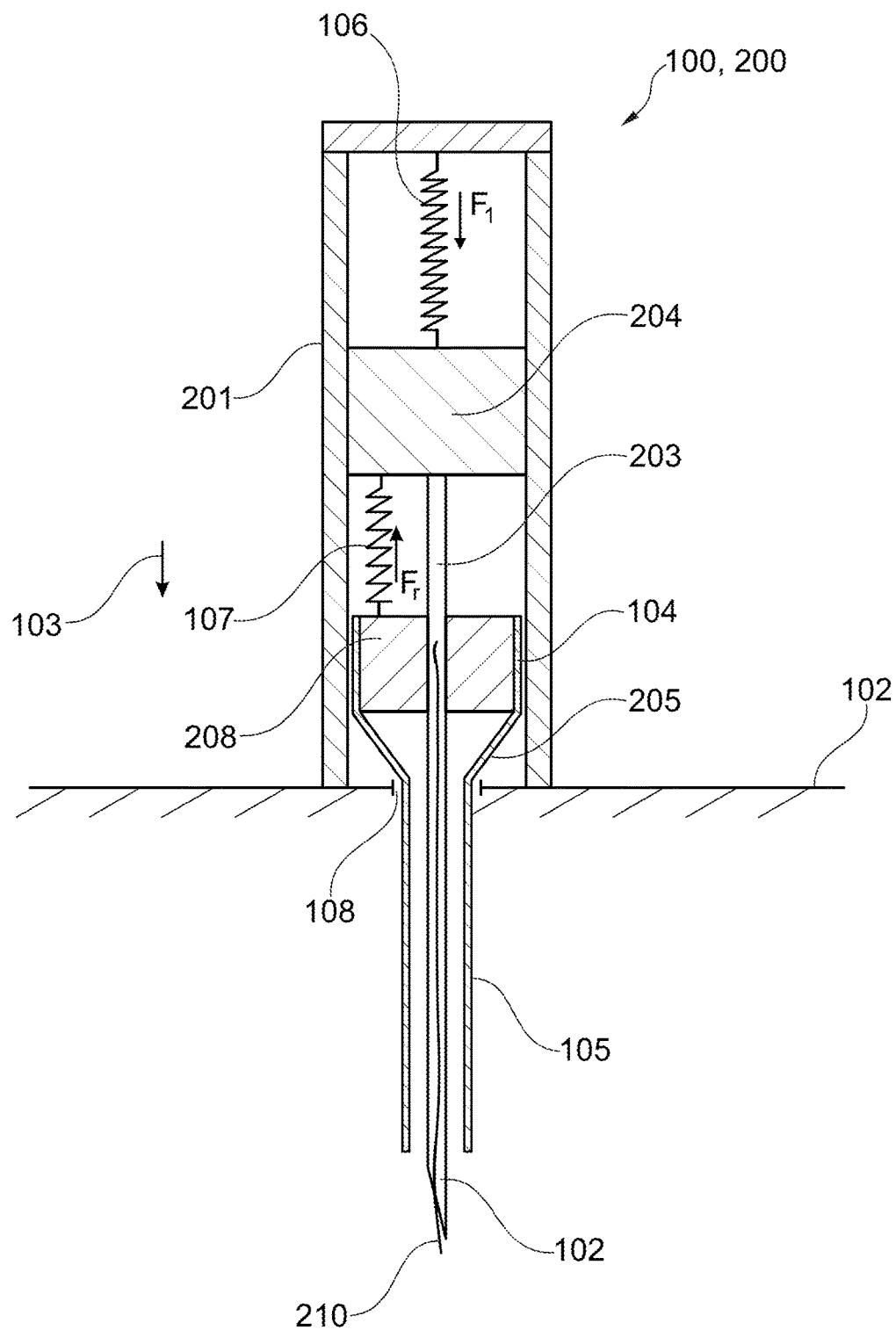
FIG. 1 shows a schematic view of a placement aid in accordance with an example form of embodiment of the present invention.

FIG. 1 shows a first example form of embodiment of the placement aid 100. The placement aid 100 comprises a main body 201 for supporting on the skin 101 of a body. The placement aid 100 also comprises a placement needle 203 and a catheter 205. The placement needle 203 is coupled to the main body 201. The placement needle 203 and the catheter 205 are arranged with regard to each other in such a way that the placement needle 203 is arranged within the catheter 205 and that a tip 102 of the placement needle 204 protrudes from a proximal end of the catheter 104 along a puncturing direction 103 so that upon placement of the catheter 205 along the puncturing direction 103 the tip 102 of the placement needle 203 penetrates the skin 101 in order to produce a skin opening 108 through which the catheter 205 is guided up to a subcutaneous end position. The catheter 205 is coupled to the placement needle 203 or by means of the placement needle 203 (indirectly) to the main body 201 in such a way that upon reaching the subcutaneous end position of the catheter 205 the placement needle 203 can be withdrawn against the puncturing direction 103 from the catheter 205 and the catheter 103 remains in the subcutaneous end position.

More particularly, FIG. 1 shows a replacement device 200 or an infusion set or replacement set, e.g. the main body 201, the piston 202 (see FIG. 2), the placement needle 203, a needle holder 204, to which the placement needle 203 is attached, and the catheter 205. The replacement device 200 is, for example, arranged in a placement device 800 (see FIG. 8) in a replaceable manner (see FIG. 8).

The placement needle 203 comprises a needle, which, for example, is made of metal or a similar hard material. With its tip 102 the placement needle produces a small cut in the skin in order to produce the skin opening 108. The skin opening 108 is widened or opened further by the remainder of the needle body and the subsequently guided catheter 205. The placement needle 203 is guided within the catheter 114.

In FIG. 1 the placement needle 203 and the catheter 205 are shown in a subcutaneous end position, i.e. at a desired depth in the skin 101 or in the tissue 109. The subcutaneous end position describes the desired position of a proximal end of the catheter 205 or the puncturing depth of the catheter 205. The subcutaneous end position can be selected in each case of application so that a proximal end of the catheter 205 is present in the fatty tissue, the muscle tissue or within a blood vessel.

As shown in FIG. 1, the main body 201 is a hollow-cylindrical body or a hollow-cylindrical tube, wherein the catheter 205 and the placement needle 203 are arranged within the main body 201. The placement needle 203 can be spatially fixed to the main body 201 or arranged in a displaceable manner at the main body 201.

If the placement needle 203 is spatially fixed to the main body 201, the user can manually move the main body 201 together with the placement needle 203 and the catheter 205 in the puncturing direction in order to puncture the skin until the subcutaneous end position is reached.

If the placement needle 203 is arranged at the main body 201 in a displaceable manner a displacement mechanism can be used. The user places the main body 201 on the skin 101 and activates the displacement mechanism so that the placement needle 203 together with the catheter 205 is moved in the puncturing direction until the subcutaneous end position is reached (see FIG. 1). The displacement mechanism is based, for example, on a spring-based mechanism. In FIG. 1 the placement needle 203 comprises a needle holder 204. The needle holder 204 is arranged within the main body 201 in a displaceable manner. Additionally, a first spring 106 is arranged between the needle holder 204 and the main body 201. The first spring 106 is set up in such a way that a first spring force F1 is exerted in the puncturing direction 103. By means of the first spring force F1 the needle holder 204 and the catheter 205 are moved along the puncturing direction 103 until the subcutaneous end position of the catheter 205 is reached. The first spring F1 can, for example, be initially pre-tensioned and held in position by means of a catch mechanism. The user can activate the displacement mechanism by releasing the first spring 106 so that the placement procedure is started.

Figure 8:
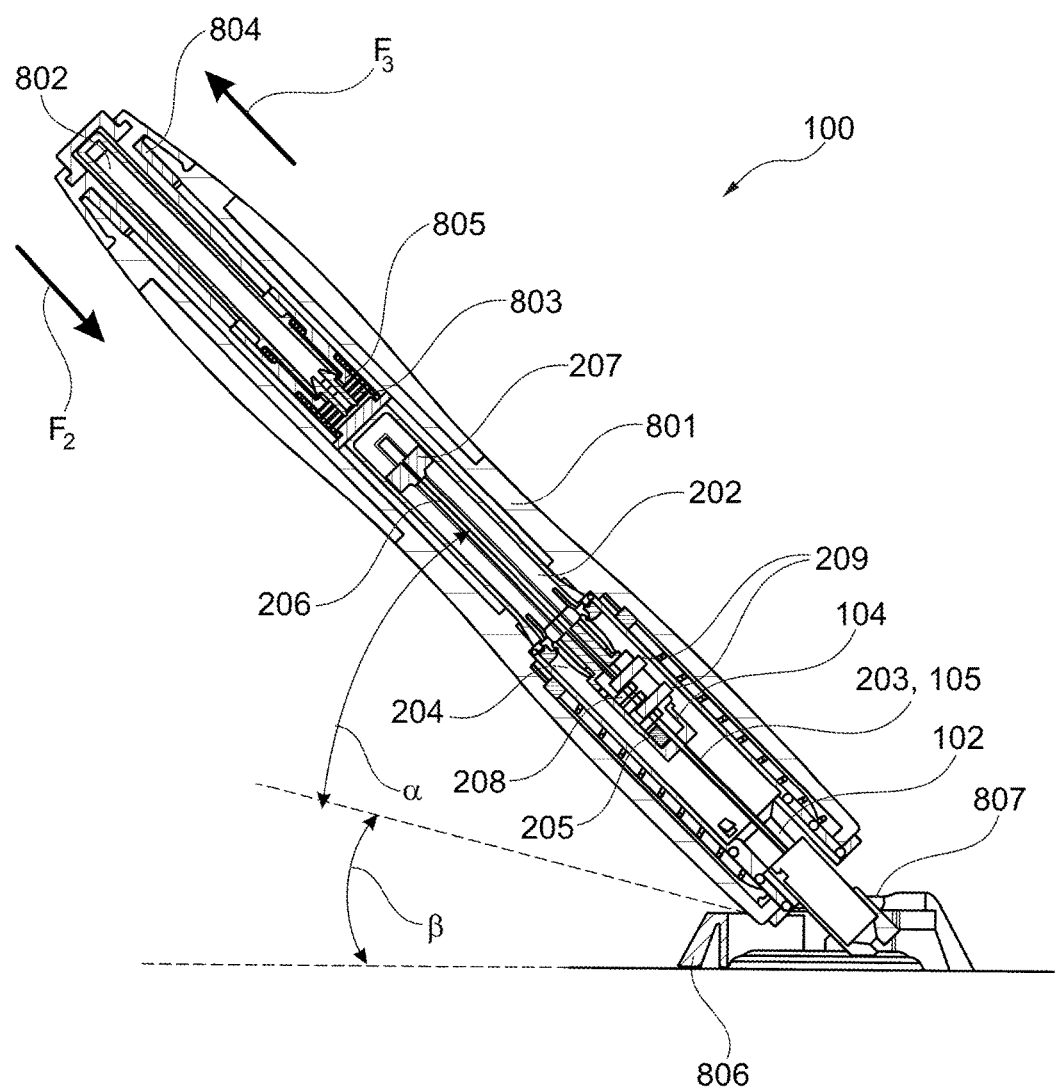
FIG. 8 to FIG. 11 show schematic cross-sectional views of a placement aid with a placement device and a replacement device in accordance with an example form of embodiment of the present invention, wherein in FIG. 8 to FIG. 11 a placement cycle is shown.
Figure 9:
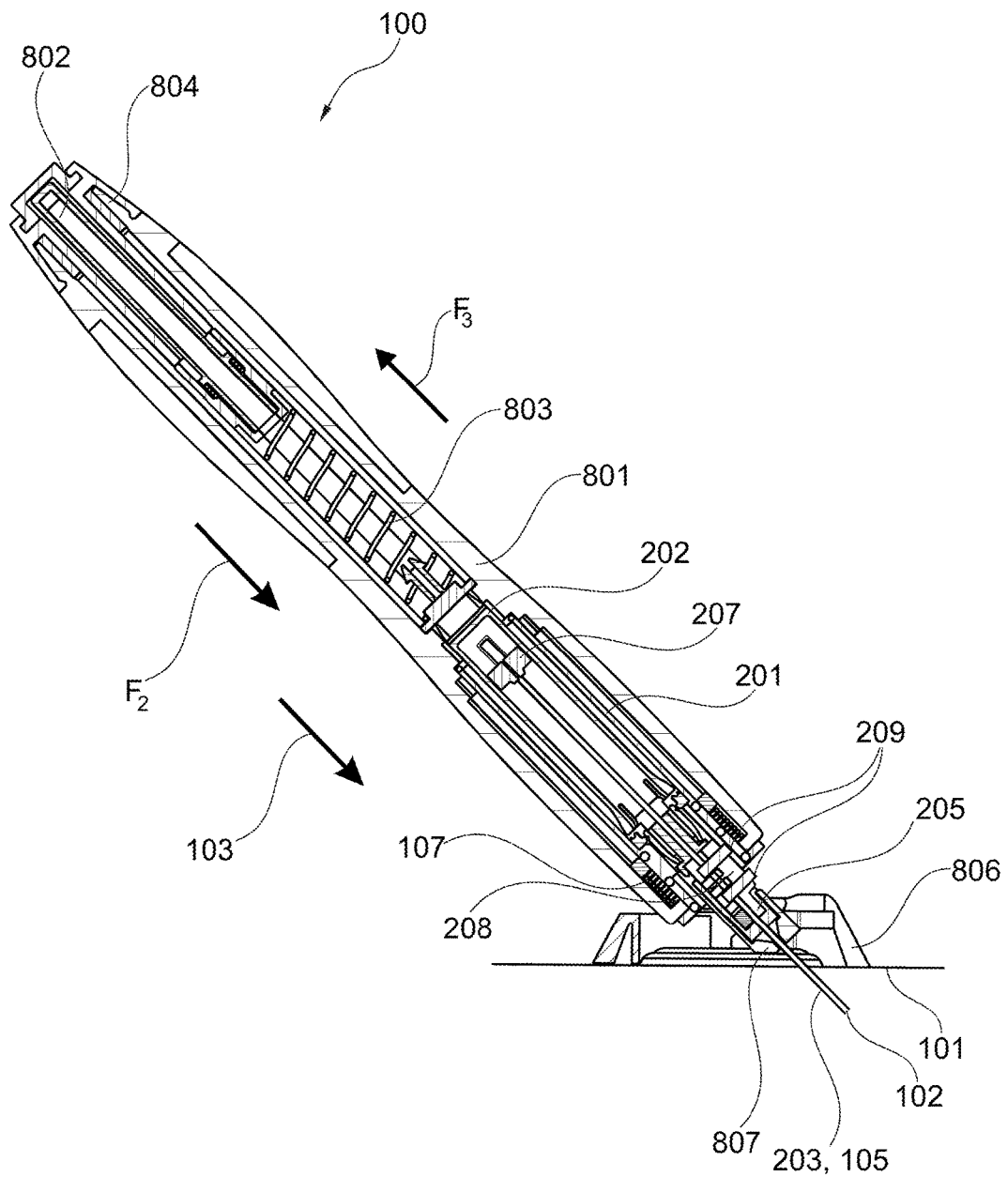
Figure 10:
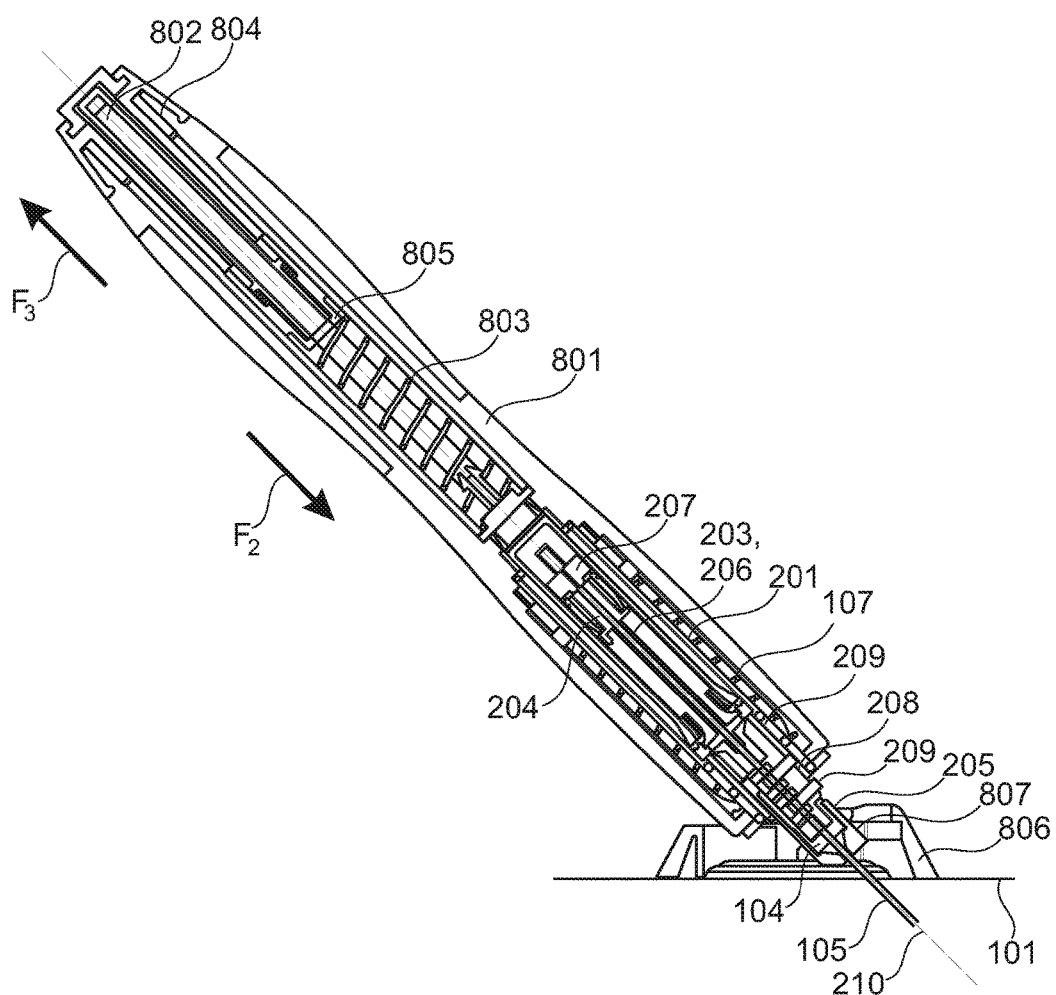
Figure 11:
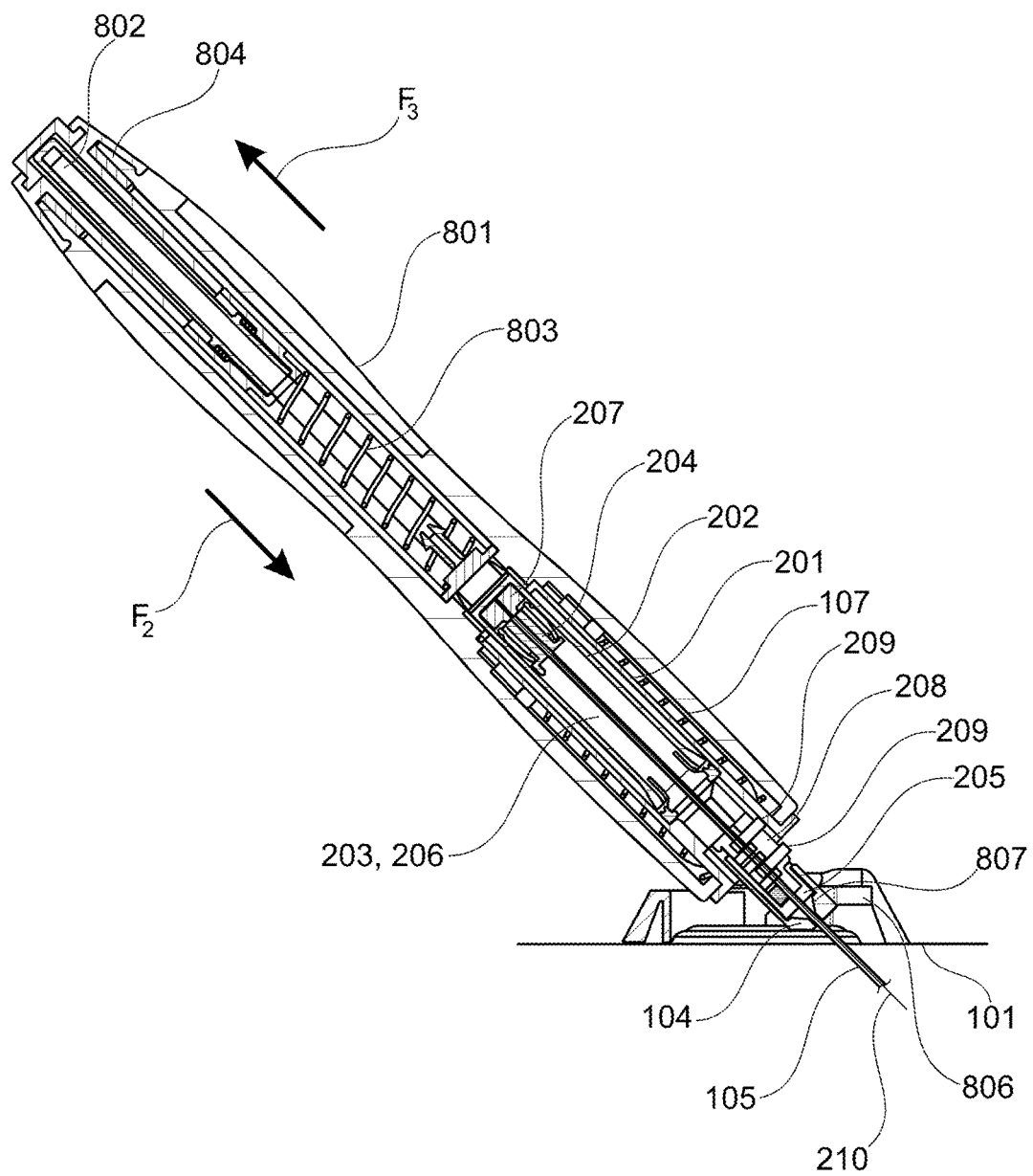

Alternatively or in addition to the first spring 106 a second spring 803, described below in FIG. 8, can be arranged between the placement device 800 of the placement aid 100 and the piston 202 of the replacement device 800 in such a way that a second spring force F2 of the second spring 803 acts along the puncturing direction 103 in order to, during the placement of the catheter 205, advance the needle holder 204 along puncturing direction 103 directly (or indirectly by means, for example, of the piston 202).

The catheter 205 is coupled to the placement needle 203 in such a way that upon reaching the subcutaneous end position of the catheter 205 the placement needle 203 can be withdrawn from the catheter 205 contrary to the puncturing direction 103 and the catheter 205 remains in the subcutaneous end position.

The placement needle 203 can, for example, be attached to the catheter 205 by means of an interlocking connection (e.g. with a hook or snap-type connection). The interlocking connection is released, for example automatically, i.e. upon reaching the subcutaneous end position, or by means of an unlocking mechanism, which can be operated by the user. Additionally, the placement needle 203 can be coupled to the catheter 205 by means of a force-fitting connection, wherein the placement needle 203 is coupled to the catheter 205 by means of frictional forces. When withdrawing the placement needle 203 the withdrawing force acting against the puncturing direction 103 exceeds the frictional force so that the placement needle 203 is released from the catheter 205 and can be pulled out. At the same time the frictional connection between the catheter 205 and the tissue surrounding the catheter 205 is larger than the withdrawing forces so that the catheter 205 remains in the subcutaneous end position.

The placement needle 203 can be withdrawn from the catheter 205 after reaching the subcutaneous end position either manually or in a spring-based manner. As shown in FIG. 1 a return spring 107 can be arranged between the needle holder 204 and a section of the main body 201. A spring force Fr of the return spring 107 presses the needle holder 204 against the puncturing direction 103. After the catheter 205 reaches the subcutaneous end position a further mechanism can release the return spring 107 so that the needle holder 204, after reaching the subcutaneous end position together with the placement needle 203, is withdrawn from the tissue contrary to the puncturing direction 103.

The catheter 205 comprises a fastening section 104, with which the catheter 205 can be attached to the placement needle 203, and a subcutaneous section 105. The subcutaneous section 105 can be at least partially introduced through the skin opening 108 into the skin 101 or tissue 109, wherein the fastening section 104 forms a (force-fitting or interlocking) connection with the placement needle 203.

The fastening section 104 can for example be a membrane or clamping element 208 made of an elastic material, such as an elastic synthetic material (e.g. a silicone pad or silicone). The placement needle 203 can, for example, puncture the clamping element so that the clamping element 208 is elastically deformed and presses against the placement needle 203 with a certain adhesive force. In this way the frictional connection between the placement needle 203 and the catheter 205 is produced. When withdrawing the placement needle 203 from the catheter 205 the predetermined adhesive force is exceeded and the placement needle 203 is pulled out while the catheter 205 remains in its position.

Further, the fastening section 104 can be used for a coupling with, for example, a support element 806 (see FIG. 8), sensor read-out units, insulin pumps or other functional devices.

A sensor wire 210 can also be arranged in the placement needle 203. The sensor wire 210 is coupled to the placement needle 203 in such a way that when placing the catheter 205 along the puncturing direction 103 the sensor wire 210 is arranged in the placement needle 203 and that upon reaching the subcutaneous end position of the catheter 205 the placement needle 203 can be pulled out from the catheter 205 against the puncturing direction 103 and the sensor wire 210 remains in the catheter 205.

The sensor wire 210 forms an electrode for example. During the placement of the catheter, the sensor wire 201 is, for example, held in position relative to the sensor needle 203 by means of a frictional connection in the sensor needle 203. Accordingly, the sensor wire 210 can be pressed against the inner surface of the placement needle 203 with a certain pressure force so that a friction force fixes the sensor wire 210 to the placement needle 203. When withdrawing the placement needle 203 the withdrawal force exceeds the frictional force fixing the sensor wire 210 to the placement needle 203 so that the placement needle 203 can be pulled out from the body relative to the sensor wire 210 and the sensor wire 210 remains in the subcutaneous end position.

After placement of the catheter 205 and the sensor wire 210 the needle holder 204 together with the placement needle 203 can be completely retracted into the inner volume of the main body 201 and is thus insulated from the surroundings of the main body 201. In this way the risk of infection from the used placement needle 203 is reduced.

FIG. 2 to FIG. 6 show perspective cross-sectional views of the replacement device 200 with a placement aid 100 according to an example form of embodiment of the present invention, wherein in FIG. 2 to FIG. 6 one placement cycle of the catheter 205 and a sensor wire 210 is shown.

The placement aid 100 in FIG. 2 to FIG. 6 essentially comprises the same features as the placement aid 100 in FIG. 1. Additionally the placement aid 100 comprises a piston 202 which can be introduced into and retracted from the main body 201 in a telescopic manner. The needle holder 204 is coupled to the piston 202 in such a way that when moving the piston 202, the needle holder 204 together with the placement needle 203 and the catheter can be advanced in the puncturing direction 103 until the subcutaneous end position is reached (see FIG. 3).

Upon reaching the subcutaneous end position the piston 202 and the needle holder 204 can be detached from one another and the needle holder 204 moves relative to the piston 202 contrary to the puncturing direction 103. The needle holder 204 thus moves into the inner volume of the piston 202 and is stored therein after placement of the catheter 205 (see FIG. 5).

Decoupling the needle holder 204 from the piston 202 can take place by means of an interlocking (e.g. snap or click-type) connection. As shown in FIG. 2 to FIG. 6, the needle holder 204 can have a notch 211 and the piston 202 can have a snap hook 212. The needle holder 204 can also be elastically deformable so that it can be pressed together at a desired position in order to release the connection between the notch 211 and the snap hook 212. For example, the needle holder 204 can have a wedge-shaped surface 213 which, upon reaching the subcutaneous end position of the catheter 205, is pushed against a stop or a further wedge-shaped surface of the main body 201. The first wedge-shaped surface can, for instances, be formed accordingly at an inner side of the main body 201. When moving the needle holder 204 along the wedge-shaped surface the needle holder 204 is compressed in the region of its wedge-shaped surface 213 so that upon reaching the subcutaneous end position of the catheter 205 the needle holder 204 is disconnected from the snap hook 213 and the needle holder 204 moves into the inner volume of the piston 202. The pushing back of the needle holder 204 against the puncturing direction 103 after reaching the subcutaneous end position of the catheter 205 can take place by means of the return spring 107 for example.

Additionally, in the placement aid 100 a holding-down rod 206 is shown in FIG. 2 to FIG. 6. The holding down rod 206 is arranged in the placement needle 203 in a displaceable manner. The holding down rod 206 is designed to frictionally press the sensor wire 210 against the placement needle 203 or the inner surface of the placement needle 203. The holding-down rod 206 can also be arranged at the main body 201 to be moved along the puncturing direction 103 so that when placing (moving) the catheter along the puncturing direction 103 the placement needle 203, the sensor wire 210 and the holding-down rod 206 can be jointly advanced to the subcutaneous end position in the tissue 109 (see FIG. 2 and FIG. 3) and that upon reaching the subcutaneous end position of the catheter 205 the holding-down rod 206 can be withdrawn from the catheter 205 contrary to the puncturing direction 103 (see FIG. 5, FIG. 6).

The holding-down rod 206 reduces the free volume inside the placement needle 203 so that the sensor wire 210 is clamped between the holding-down rod 206 and the inner surface of the placement needle 203. In this way the holding-down rod 206 produces the pressing force of the sensor wire 113 on the inner surface of the placement needle 203. In particular, in this way the placement needle 203 can be withdrawn from the body without the holding-down rod 206 and the sensor wire 210 being pulled out so that they remain in the subcutaneous end position (cf. FIG. 4 with FIG. 5). Only after the placement needle 203 has at least partially been withdrawn from the body, the holding rod 206 can be removed from the body in a subsequent procedure and only the sensor wire 210 together with the catheter 205 remains in the body 205.

This staggered removal of the placement needle 203 and the holding-down rod 206 is achieved in that the plunger 207 of the holding-down rod 206 is frictionally connected to the piston 202. The plunger 207 is arranged in the piston 202 in such a way that in a predetermined position in the piston 202 the needle holder 204 is pressed against the plunger 207 contrary to the puncturing direction 103 in such a way that the frictional connection between the piston 202 and the plunger 207 is overcome and the plunger 207 with the holding-down rod 206 is pushed against the puncturing direction 103 relative to the piston 202 by means of the needle holder 204 (see FIG. 5, FIG. 6).

The predetermined position of the plunger 207 in the piston 202 is selected in such a way that the needle holder 204 initially withdraws the placement needle 203 from the body and presses against the plunger 207 only after the needle holder 204 has already been moved a certain distance in the piston 202 contrary to the puncturing direction 103. Thus, the holding-down rod 206 initially remains on the subcutaneous end position in the body along with the sensor wire 210, whereas a section of the placement needle 203 has already been withdrawn from the body.

Figure 2:
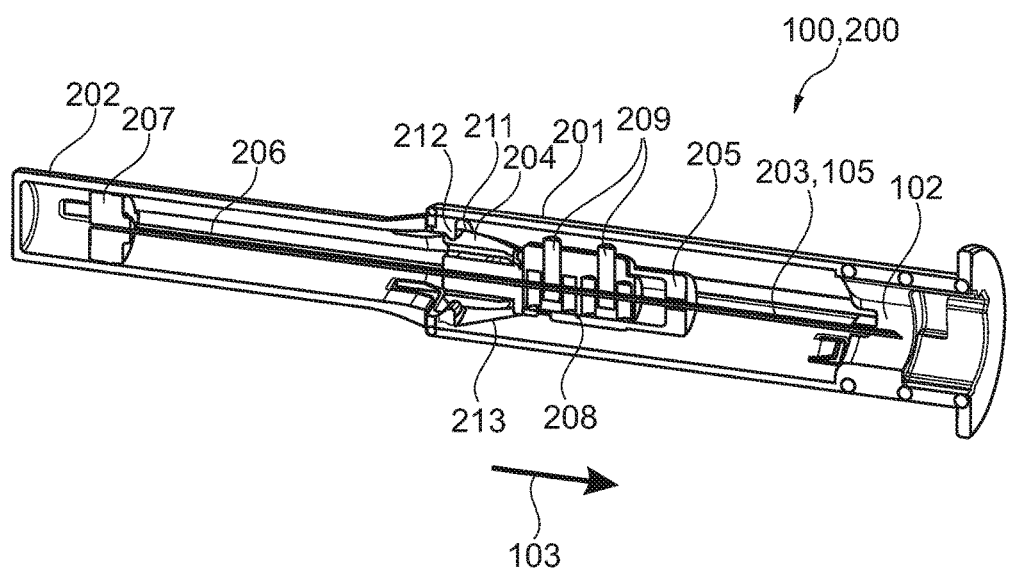
FIGS. 2 to 6 show schematic cross-sectional views of a replacement device of a placement aid in accordance with an example form of embodiment of the present invention, where in FIG. 2 to FIG. 6 one placement cycle is shown.
Figure 3:
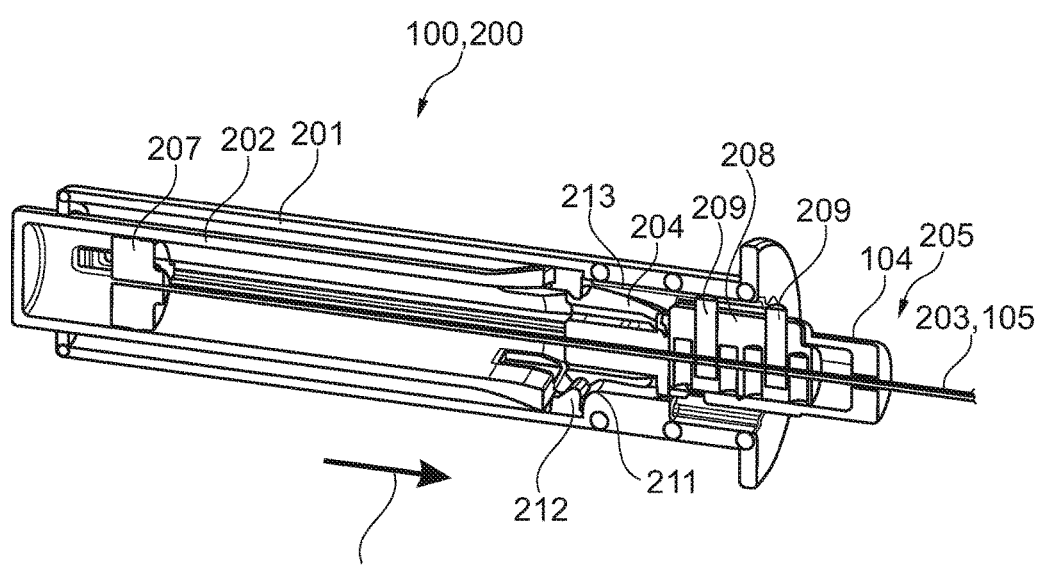
Figure 4:
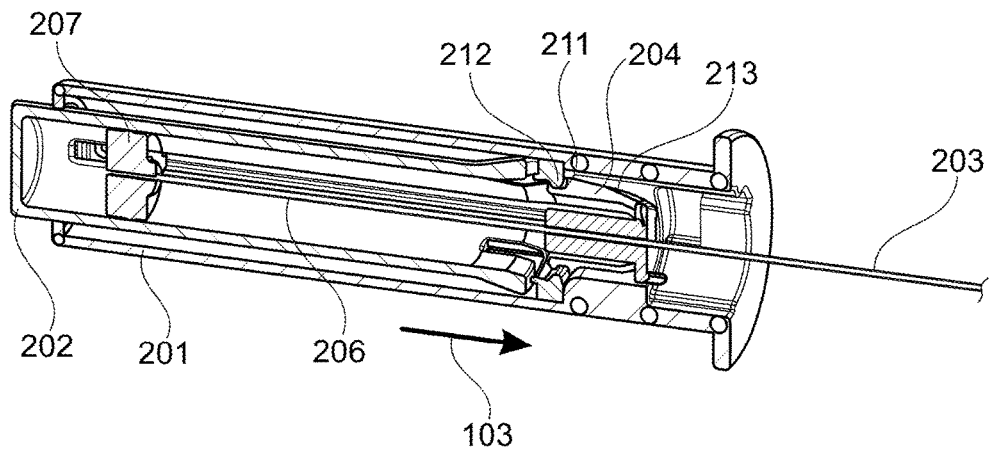
Figure 5:
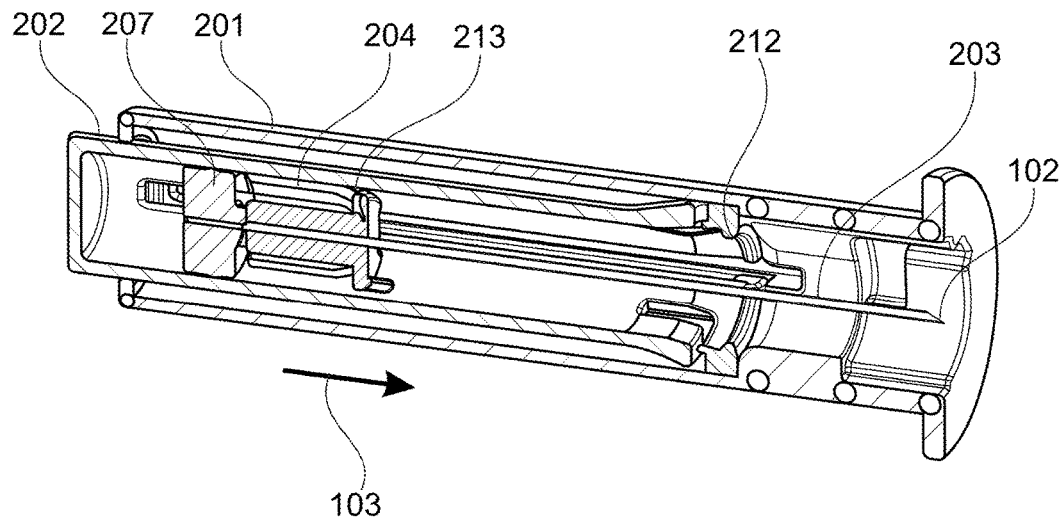
Figure 6:
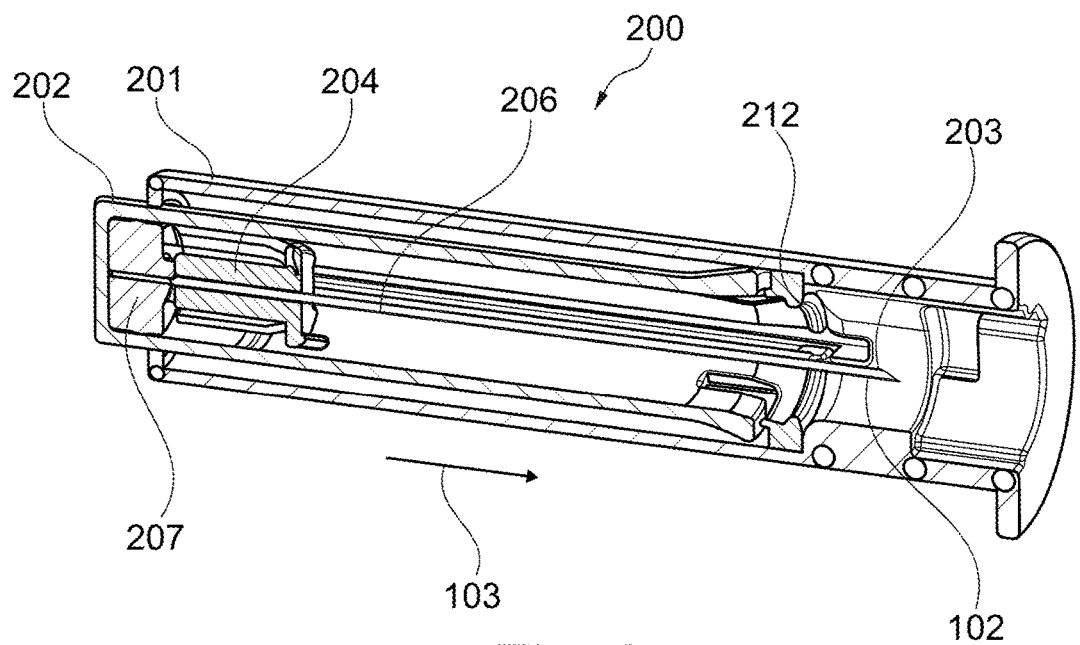

Furthermore, in FIG. 2 and FIG. 3 the catheter 205 is shown with the fastening section 104 and the subcutaneous section 105. The clamping element 208 is arranged in the fastening section 104. The clamping element 208 also comprises at least one contact surface 209. The contact surface 209 is, for example, itself elastically deformable or attached in the elastically deformable clamping element 208. The placement needle 203, which contains the sensor wire 210 within it, penetrates the elastically deformable clamping element 208. After the placement needle 203 has been withdrawn from the elastically deformable clamping element 208 and, accordingly, the catheter 205, the elastically deformable clamping element 208 closes the hole through which the placement needle 203 penetrated. After withdrawal of the placement needle 203 the sensor wire 210 is still located in this hole and the contact surface 209 presses on the contact wire 210 so that a conductive contact between the sensor wire 210 and the contact surfaces 209 is produced. Additionally, the contact surfaces 209 can be connected to a sensor read-out unit so that measuring signals of the sensor wire 113 can be read out.

Figure 7:
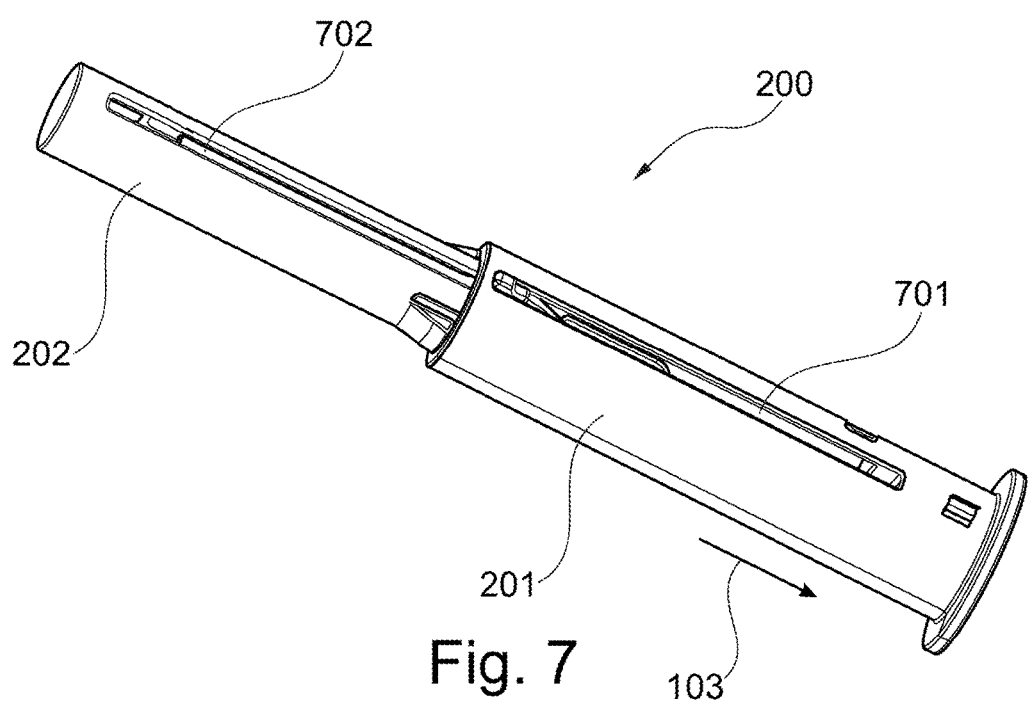
FIG. 7 shows a perspective view of a replacement device of the placement aid in FIG. 2 to FIG. 6.

FIG. 7 shows a perspective view of the placement aid 100 in FIG. 2 to FIG. 6. The placement aid 100 shows the piston 202 and the main body 201 in an initial position. The main body 201 comprises a first gap/groove 701 which extends along the puncturing direction 103. In this first gap 701 the piston 202 can, for example, be movably guided (e.g. by means of guide bolts of the piston 202 guided in the first gap 701). The piston 202 comprises, for example, a second gap 702 which extends along the puncturing direction 103. In this second gap 702 the needle holder 702 can for example be movably guided (e.g. by means of guide bolts of the needle holder 204 guided in the second gap 702).

FIG. 8 to FIG. 11 show perspective cross-sectional views of an placement aid 100 with a placement device 800 in accordance with an example form of embodiment of the present invention, wherein in FIG. 8 to FIG. 11 a placement cycle of the catheter 205 and the sensor wire 210 is shown.

The placement aid 100 in FIG. 8 to FIG. 11 exhibits essentially the same features as in the placement aid 100 in FIG. 2 to FIG. 7. The replacement device 200 comprises the main body 201, the piston 202, the placement needle 203, the needle holder 204, to which the placement needle 204 is fastened, the sensor wire 210, and the catheter 205, wherein the replacement device 200 is arranged in the placement device 800 in a replaceable manner.

In particular, the piston 202 and the main body 201 can be used in a replaceable manner in the placement device 800. The placement aid 100 comprises a hollow-cylindrical housing, for example.

The placement aid 100 comprises, for example, a displacement mechanism for moving the piston 202, the placement needle 203 and the catheter 205. A second spring is arranged between the placement device 800 and the piston 202 of the replacement device 800 in such a way that a second spring force F2 of the second spring 803 acts along the puncturing direction 103 in order to, during the placement of the catheter 205, directly move the needle holder 204 along the puncturing direction 103 (or indirectly by means, for example, of the piston 202).

During a displacement of the needle holder 205 against the puncturing direction 103 the second spring 803 is pre-tensioned. If, for example, the needle holder 204 is inserted into the placement device 800 along with the piston 202 and/or main body 201, during placement into the placement device 800 the second spring 803 can be automatically pre-tensioned. In this way the placement aid 100 is simply loaded a prepared for use.

A locking element 805 (e.g. a locking hook) locks the piston in an initial position in which the second spring 803 is pre-tensioned. A trigger device 802 (e.g. pushbutton) is connected to the locking element 805 in such a way that upon operation of the trigger element 802, for example by a user, the locking element 805 releases the piston 202 and the piston 202 can be advanced with the needle holder 204 along the puncturing direction 103 by means of the second spring force F2 (cf. FIG. 8 with FIG. 9). With a third spring force F3 a third spring 804 can move the trigger element 802 back into a starting position.

Upon reaching the subcutaneous end position of the catheter 205 (FIG. 9 to FIG. 11), by means of the return spring 107 the placement needle 203 is decoupled from the catheter 205 and is removed from the body against the puncturing direction 103. In interaction with the second spring 803 an automatic placement mechanism is thus provided. The user only has to operate, for example, the trigger element 802 in order to activate the placement aid 100. After operation of the trigger element 802 the piston 202 with the needle holder 204 and with the placement needle 203 together with the catheter 205 moves to the subcutaneous end position. The needle holder 204 is then removed from the body by way of the return spring 107 without the user having to take any further steps.

Further, the main body 201 is attached in a replaceable manner to a support element 806 in such a way that the main body 201 is fixed between the placement needle 203 and the skin surface at a predetermined puncturing angle. The support element 806 can, for example, be attached to the skin 101 by means of an adhesive connection (e.g. by means of a plaster). The support element 806 comprises coupling elements, for example, which couple the main body 201 to the support element 806 in a replaceable manner. For example, the main body 201 can be fastened to the support element 806 by means of a bayonet connection.

The support element 806 further comprises a fastening element or a catheter element 807 which is designed to connect the catheter 205 to the support element 806 when the catheter 205 is in the subcutaneous end position.

The catheter holder 807 forms with the catheter 205 for instance a force-fitting or interlocking connection (e.g. a snap-hook connection). For example, the catheter holder 807 can form a bayonet connection with the catheter 205.

The catheter holder 807 is, for example, arranged in a pivoting manner in the support element 806 and can be selectively locked in a desired pivoting position. The user can adjust the desired pivoting position in such a way that the catheter holder 807 holds the catheter 205 or the trigger device 200 and the placement device 800 in such a way that a desired first or second puncturing angle α, β can be set.

The puncturing angle α, β defines an angle between the skin surface and the longitudinal axis of the placement needle 203. The puncturing angle α, β is, for example, between 0° and 90°. The shallower the angle the closer the subcutaneous end position is to the skin surface. The steeper the angle, for example around 90°, the deeper the subcutaneous end position is within the skin or the tissue.

By means of being able to select the puncturing angle α, β the user can adapt the puncturing angle α, β to the thickness of his/her subcutaneous fat layer so that with a given catheter and sensor wire length the proximal ends of the catheter 205 and sensor wire 210 come to rest in the fatty tissue and do not extend into the underlying muscle tissue. The replacement set or the replacement device 200 can therefore advantageously be produced with a single catheter and sensor wire length.

Upon reaching the subcutaneous end position the catheter 205 is decoupled from the main body 201. Accordingly, the main body 201 can be detached from the support element 806, wherein the catheter 205 remains fixed at the support element 806 and can be separated from the main body 201.

Figure 12:
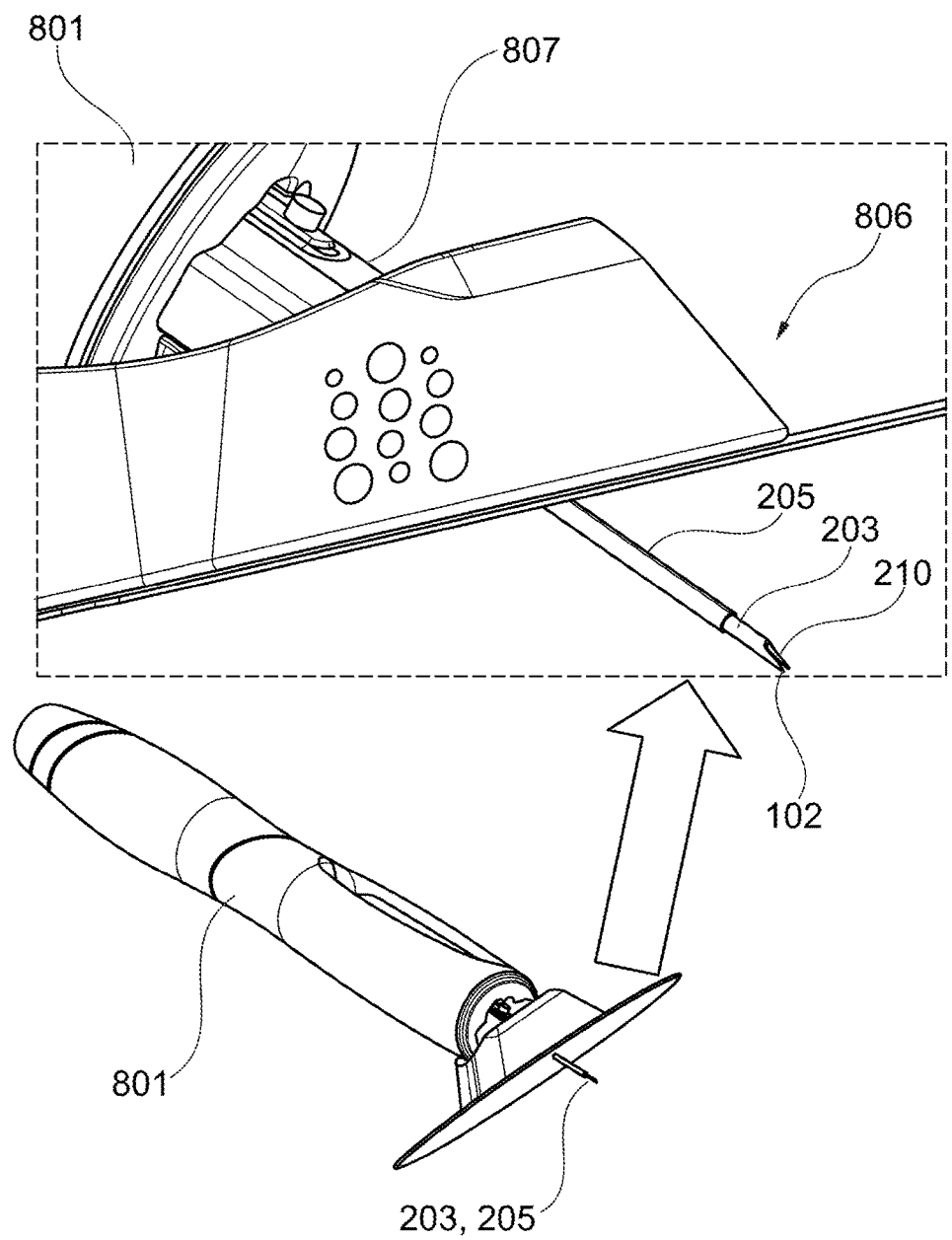
FIG. 12 shows a perspective view of the placement aid in FIG. 8 to FIG. 11.

FIG. 12 shows a perspective view of the placement aid 100 in FIG. 8 to FIG. 11.

Figures 13, 14, 15:
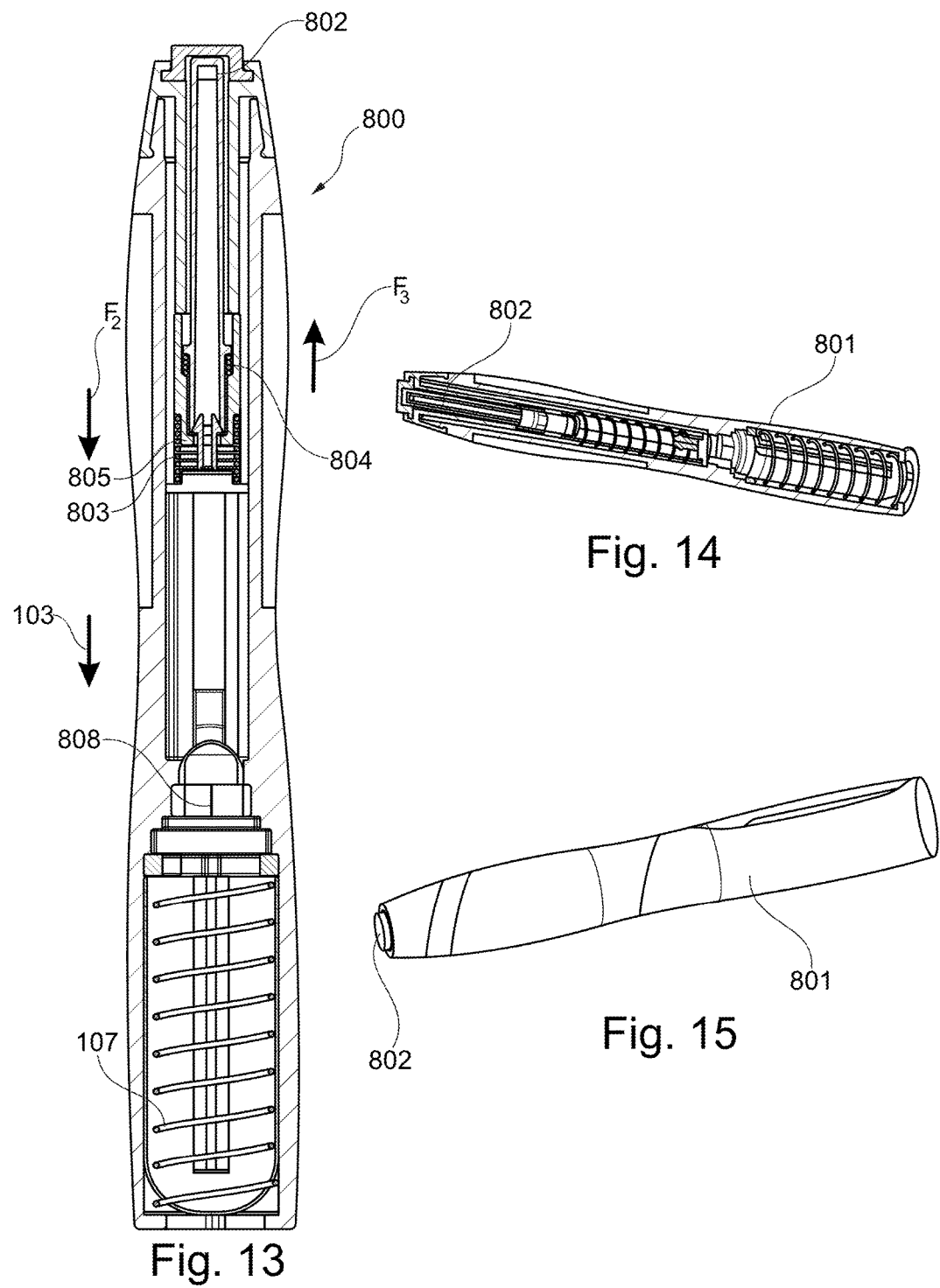
FIG. 13 to FIG. 15 show schematic representations of a housing body or a placement device according to an example form of embodiment of the present invention.

FIG. 13 to FIG. 15 show schematic representations of the housing body 801. The placement aid 100 comprises a hollow cylindrical shape. The trigger element 802 is arranged in a head region of the housing body 801. The trigger element 802 comprises a hollow-cylindrical form, wherein the trigger element 802 comprises an opening in the interior of the housing body 801. Upon displacement of the trigger element 802 in the puncturing direction 103 the trigger element 802 is pulled over the locking elements 805. The locking elements 805 are thereby pressed together and the second spring 803 is released. In this way the second spring 803 can exert the second spring force F2 on the piston 22 and move it in the puncturing direction 103. In FIG. 13 a return ring 808 is shown in which the piston 202 can be fastened in a replaceable manner. After operation of the trigger element 802, by way of the third spring force F3 the third spring 804 again presses the trigger element 802 into a starting position.

FIG. 16 shows a procedure for fastening the placement device 800 to the replacement device 200, i.e. the main body 201 and the piston 202. The placement device 800 can be connected to the main body 201 of the replacement device 200 by means of a bayonet connection for example. In this way the piston 202 together with the main body 201 can be pushed into the housing 801 and fastened by way of a quarter or half turn. Accordingly, after placement of the sensor wire the piston 202 and the main body 201 can be detached from the placement device 800 by way of a quarter or a half turn. Accordingly, after placing the sensor wire, the piston 202 and the main body 201 can be removed from the placement device 800 by means of a quarter or half turn.

The main body 201 can, for example, be connected to the support element 806 by mean of a bayonet connection. After placing the catheter 205 and the sensor wire 210 these remain fixed in the support element 806. The placement device 800 together with the replacement device 200 (more particularly with the main body 201 and the piston 202) can be detached from the support element 806. The catheter holder 807 can for example be attached to the support element 806 in a pivotable manner in order to adjust the puncturing angle.

After the catheter 205 has been brought into the subcutaneous end position and has been fastened to the support element 806, the catheter 205 can be used for the further application. For example, at the sensor wire 210 the sensor read-out unit or a pump unit can be subsequently fastened to the catheter 205 for an infusion of a medication.

The sensor read-out unit can be replaceably attached to the support element 806 in such a way that the senor read-out unit is coupled for signal exchange with the sensor wire 210, which is located in the catheter 205. Accordingly, a pump unit can be replaceably attached to the support element 806 in such a way that the pump unit is coupled to the catheter 205 so that a medication can be infused by the pump unit into the catheter 205 and thus be conveyed to the subcutaneous end position.

FIG. 17a to FIG. 17c show schematic views of a support element 806 with an adjustable catheter holder 807. The catheter holder 807 is attached to the support element in a pivotable manner and can be locked or fixed in a desired pivoting position. The catheter 205 can be fixed in the catheter holder 807. In this way a desired puncturing angle α, β can be set by means of the catheter holder 807.

FIG. 17C further shows that the catheter holder 807 can be folded into the support element 806 and is thus protected from surrounding influences. In the catheter holder 807 the catheter can be arranged isolated from the placement aid 100. The catheter 205 can thus initially be placed by means of the placement aid 100 and the placement aid 100 is then detached from the catheter 205 so that the catheter 205 is present in the catheter holder 807. If no medication is supplied or no measurement is carried out by means of the sensor wire 210, the catheter 205 together with the catheter holder 807 can be pivoted into the inactive, protected position, as shown in FIG. 17C.

It is additionally pointed out that "comprising" does not rule out other elements or steps and "a" or "an" does not rule out a plurality. It is also pointed out that features or steps described with reference to one of the above examples of embodiment can also be used in combination with other features or steps of other examples of embodiment described above. Reference numbers in the claims should not be seen as restrictive.

LIST OF REFERENCE NUMBERS

100 Placement aid
101 Skin/tissue
102 Tip
103 Puncturing direction
104 Fastening section
105 Subcutaneous section of the catheter
106 First spring
107 Return spring
108 Skin opening
109 Skin
200 Replacement device
201 Main body
202 Piston
203 Placement needle
204 Needle holder
205 Catheter
206 Holding-down rod
207 Plunger
208 Clamping element
209 Sensor contact
210 Sensor wire
211 Notch
212 Snap hook
213 Wedge-shaped surface
701 First gap
702 Second gap
800 Placement device
801 Housing body
802 Trigger element
803 Second spring
804 Third spring
805 Locking element
806 Support element
807 Catheter holder
808 Return ring
F1 First spring force
F2 Second spring force
F3 Third spring force
Fr Return spring force
α,β Puncturing angle

The invention claimed is:

1. A placement aid for placing a catheter and a sensor wire into a body comprising:
a placement device;
a replacement device with a main body, a placement needle, a catheter and a sensor wire;
wherein the replacement device is arranged in the placement device in an interchangeable and replaceable manner,
wherein the placement needle is coupled to the main body,
wherein the placement needle and the catheter are arranged with regard to each other in such a way that the placement needle is arranged within the catheter, and that a tip of the placement needle protrudes from a proximal end of the catheter along a puncturing direction so that upon placement of the catheter along the puncturing direction, the tip of the placement needle penetrates a skin in order to produce a skin opening through which the catheter can be guided up to a subcutaneous end position, and wherein the sensor wire is coupled to the placement needle in such a way that upon placement of the catheter along the puncturing direction, the sensor wire is arranged in the placement needle and that, upon reaching the subcutaneous end position of the catheter, the placement needle can be removed from the catheter against the puncturing direction and the sensor wire remains in the catheter; and
a holding-down rod which is arranged in the placement needle in a displaceable manner,
wherein the holding-down rod is designed to frictionally press the sensor wire against the placement needle, and
wherein the holding-down rod is further arranged at the main body in a movable manner along the puncturing direction such that, upon placement of the catheter along the puncturing direction, the placement needle, the sensor wire and the holding-down rod can jointly be advanced up to the subcutaneous end position of the catheter and such that, upon reaching the subcutaneous end position of the catheter, the holding-down rod can be withdrawn from the catheter against the puncturing direction.

2. The placement aid according to claim 1,
wherein the replacement device further comprises a piston and a needle holder, to which the placement needle is attached,
wherein the piston is arranged in the main body in a displaceable manner,
wherein the needle holder with the placement needle is arranged at the main body so as to be displaceable along the puncturing direction,
wherein the needle holder is coupled to the catheter in such a way that, upon placement of the catheter, the needle holder advances the catheter along the puncturing direction, and
wherein the piston is coupled to the needle holder in such a way that the needle holder can be advanced along the puncturing direction by means of the piston.

3. The placement aid according to claim 2, further comprising a first spring which is arranged between the main body and the needle holder in such a way that a first spring force of the first spring acts along the puncturing direction in order to advance the needle holder along the puncturing direction relative to the main body upon the placement of the catheter.

4. The placement aid according to claim 2, wherein the piston is designed to be introduced into and retracted from the main body in a telescopic manner.

5. The placement aid according to claim 2, wherein the piston is detachably coupled to the needle holder in such a way that, upon reaching the subcutaneous end position of the catheter, the needle holder can be decoupled from the piston and the needle holder can be moved relative to the piston against the puncturing direction.

6. The placement aid according to claim 2, further comprising a spring which is arranged between the placement device and the replacement device in such a way that a spring force of the spring acts along the puncturing direction in order to advance the needle holder along the puncturing direction upon placement of the catheter.

7. The placement aid according to claim 6, wherein the spring is set up in such a way that, when the needle holder is moved against the puncturing direction, the spring can be pre-tensioned.

8. The placement aid according to claim 6,
wherein the placement device comprises a locking element and a trigger element, wherein the locking element locks the needle holder in an initial position, in which the spring is pre-tensioned, and wherein the trigger element is coupled to the locking element in such a way that, when operating the trigger element, the locking element releases the needle holder and the needle holder can be advanced along the puncturing direction by means of the spring force.

9. The placement aid according to claim 8, further comprising an additional spring which is arranged between the placement device and the replacement device in such a way that a spring force of the additional spring acts against the puncturing direction in order to displace the trigger element and the locking element back into their respective initial position.

10. The placement aid according to claim 6,
wherein the piston is arranged in the placement device in a displaceable manner, and
wherein the piston is coupled to the spring and to the needle holder in such a way that the piston and the needle holder can be advanced along the puncturing direction by means of the spring force.

11. The placement aid according to claim 2, further comprising a return spring which is arranged between the placement device and the needle holder in such a way that return force of the return spring acts against the puncturing direction in order to advance the needle holder against the puncturing direction after placement of the catheter.

12. The placement aid according to claim 11, wherein the return spring is set up in such a way that when the needle holder moves along the puncturing direction, the return spring can be pre-tensioned.

13. The placement aid according to claim 1,
wherein a clamping element is arranged in a fastening section of the catheter, and
wherein the clamping element forms a force-fitting connection with the placement needle.

14. The placement aid according to claim 1, wherein the holding-down rod is further arranged at the main body in such a way that upon reaching the subcutaneous end position of the catheter, the holding-down rod can be withdrawn from the catheter after the placement needle has at least partially been pulled out of the catheter.

15. The placement aid according to claim 14,
wherein the holding-down rod comprises a plunger which is attached to the piston by mean of a force-fitting connection, and
wherein the plunger is further arranged in the piston in such a way that, at a predetermined position in the piston, the needle holder presses against the plunger against the puncturing direction in such a way that the force-fitting connection between the piston and the plunger can be overcome and the plunger with the holding-down rod can be moved by means of the needle holder against the puncturing direction relative to the piston.

16. The placement aid according to claim 1, further comprising a support element which can be attached to the skin,
wherein at least one of the main body and the placement device can be attached to the support element in a replaceable manner in such a way that the main body can be affixed with a predetermined puncture angle between the placement needle and the skin.

17. The placement aid according to claim 16, wherein the support element comprises a fastening element which is designed to fasten the catheter to the support element when the catheter is in the subcutaneous end position.

18. The placement aid according to claim 16, further comprising at least one of a sensor read-out unit, which can be attached in a replaceable manner to the support element in such a way that the sensor read-out unit is coupled to the sensor wire; and
a pump unit for injecting a medication, wherein the pump unit can be attached at the support element in a replaceable manner in such a way that the pump unit is coupled to the catheter.

19. A method of placing a catheter in to a body with a placement aid according to claim 1, wherein the method comprises:
arranging the replacement device in the placement device;
applying the placement aid on a skin of the body;
placing the catheter by means of the placement aid; and
removing and replacing the replacement device from the placement device.

* * * * *